United States Patent [19]

Rauscher et al.

[11] Patent Number: 4,544,631
[45] Date of Patent: Oct. 1, 1985

[54] PROCESS AND REAGENT FOR THE DETERMINATION OF α-AMYLASE

[75] Inventors: Elli Rauscher, Munich; Ulrich Neumann, Peissenberg; August W. Wahlefeld, Weilheim; Alexander Hagen, Tutzing; Wolfgang Grüber, Tutzing-Unterzeismering; Joachim Ziegenhorn, Unterpfaffenhofen; Eugen Schaich, Weilheim; Ulfert Deneke, Peissenberg; Gerhard Michal; Günter Weimann, both of Tutzing, all of Fed. Rep. of Germany

[73] Assignee: Boehringer Mannheim GmbH, Mannheim-Waldhof, Fed. Rep. of Germany

[21] Appl. No.: 311,856

[22] Filed: Oct. 16, 1981

Related U.S. Application Data

[63] Continuation of Ser. No. 941,934, Sep. 11, 1978, abandoned.

[30] Foreign Application Priority Data

Sep. 13, 1977 [DE]  Fed. Rep. of Germany ....... 2741192
Dec. 14, 1977 [DE]  Fed. Rep. of Germany ....... 2755803

[51] Int. Cl.$^4$ .................. C12Q 1/54; C12Q 1/48; C12Q 1/40; C12Q 1/34; C12Q 1/32
[52] U.S. Cl. ........................................ 435/14; 435/15; 435/22; 435/18; 435/26; 435/810; 435/805
[58] Field of Search ................. 435/22, 25, 28, 26, 435/14, 805, 810, 15, 18

[56] References Cited

U.S. PATENT DOCUMENTS

| | | | |
|---|---|---|---|
| 3,867,259 | 2/1975 | Forgione | 435/26 |
| 3,886,045 | 5/1975 | Meiattini | 435/28 |
| 4,000,042 | 12/1976 | Adams | 435/22 |
| 4,036,697 | 7/1977 | Pierre et al. | 435/22 |
| 4,059,407 | 11/1977 | Hochstrasser | 435/22 |
| 4,071,407 | 1/1978 | Hall | 435/22 |
| 4,081,326 | 3/1978 | Hall | 435/22 |
| 4,101,381 | 7/1978 | Klose et al. | 435/14 |
| 4,102,747 | 7/1978 | Driscoll et al. | 435/22 |
| 4,233,403 | 11/1980 | Menson et al. | 435/22 |
| 4,237,221 | 12/1980 | Gauhl et al. | 435/22 |

Primary Examiner—Esther M. Kepplinger
Attorney, Agent, or Firm—Felfe & Lynch

[57] ABSTRACT

α-Amylase is determined by the enzymatic splitting of an α-amylase substrate and measurement of a fission product, wherein there is used as a substrate a maltoheptaose compound of the formula

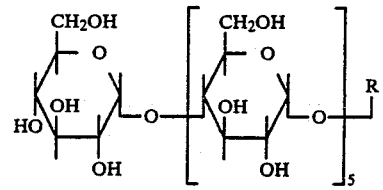

wherein R is a glucoside, phenylglucoside, mononitrophenylglucoside, dinitrophenylglucoside, sorbitol or gluconic acid group. Reagents comprising such a substrate and a system for the determination of a fission product formed from the amylase substrate by α-amylase, are also provided.

19 Claims, 1 Drawing Figure

Fig.1

PROCESS AND REAGENT FOR THE DETERMINATION OF α-AMYLASE

This is a continuation of Ser. No. 941,934, filed Sept. 11, 1978, now abandoned.

The present invention is concerned with a process and a reagent for the determination of α-amylase.

The determination of α-amylase in serum is an important clinical parameter for the function of the pancreas. The commercially available reagents for the determination of α-amylase are preponderantly based upon a system in which starch is broken down by α-amylase and the fragments formed are determined in the visible range of light or in the UV range, depending upon whether color starch or native starch is used in the test as the substrate for the amylase. An important disadvantage of these processes and reagents is that starch, which is a macromolecule, cannot be sufficiently standardised and characterised so that the rate of reaction of individual batches can vary very greatly and, when carrying out measurements, a standard must always be included. For better results, a more uniform substrate would be necessary which provides dependable results in the case of fission.

A step forwards in the direction of a more uniform substrate occurred with the use of maltopentaose. This is split by α-amylase into maltotriose and maltose and maltotriose and maltose are converted by α-glucosidase into glucose which can then be determined by any desired method, for example by the known hexokinase method.

Besides maltopentaose, it has also already been proposed to use maltotetraose and maltohexaose as substrate (see U.S. Pat. Nos. 3,879,263 and 4,000,042). However, in this case, the results obtained with the tetraose were markedly poorer than those obtained with the pentaose and with hexaose even worse results were obtained than with the tetraose. Thus, in the case of maltotetraose and -pentaose, it is still possible to obtain a stoichiometric reaction whereas in the case of the hexaose, just still tolerable deviations from the stoichiometric reaction were ascertained.

A disadvantage of maltopentaose, which was also found in the case of the tetraose, is, however, that a considerable reagent blank occurs, i.e. the measurement reaction already starts before the sample to be determined is added. Furthermore, this reagent blank is not constant in the case of comparatively high substrate concentrations but rather changes for more than 25 minutes before a constancy of this side reaction is achieved.

It has also been ascertained that the assumed different fission of maltopentaose by pancreas α-amylase and saliva α-amylase, which would have enabled a differentiation, does not actually exist (see *J. BC.*, 1970, 245, 3917–3927; *J. Biochem.*, 51, p. XVIII, 1952).

The present invention provides a process and a reagent for the determination of α-amylase in which a substrate is used which has a higher degree of purity and uniformity than the known substrates, is readily obtainable and satisfies the requirements with regard to the blank value without serum, the length of the lag phase and the achievable maximum activity. Furthermore, a simple measurement without expensive and complicated apparatus is to be possible and a suitability for rapid diagnostics, such as test strips, is to be provided.

The process of the invention for the determination of α-amylase by the enzymatic fission of an α-amylase substrate and measurement of a fission product essentially comprises using, as substrate, a compound of the general formula:

in which R is a glucoside, phenylglycoside, mononitrophenylglucoside, dinitrophenylglucoside, sorbitol or gluconic acid group.

We have, surprisingly, found that maltoheptaose possesses superior properties as a substrate for α-amylase, although in the case of the oligomaltoses from maltopentaose to maltohexaose, which have already been suggested for this purpose, a decrease in suitability has been ascertained since the maltohexaose gives results which are substantially poorer than those achieved with the pentaose. Therefore, it was to have been expected that with a further lengthening of the maltose oligosaccharide chain, no longer tolerable errors would occur. Surprisingly, however, better results are achieved than with the pentaose. Thus, for example, the reagent blank value in the case of 0.02 ml. of sample with maltopentaose as substrate amounts to 73% but with maltoheptaose amounts to only 13%, referred to the end-point of the determination.

Furthermore, we have found that instead of maltoheptaose itself, certain maltoheptaose derivatives can also be employed which, by the action of α-amylase, form a derivatised fission product which can be determined especially advantageously.

The process according to the present invention is especially suitable for the determination of the fission products by means of α-glucosidase or maltose phosphorylase.

In the case of the determination with α-glucosidase and a compound of general formula (I) in which R is a glucoside group, the fission products of the maltoheptaose, i.e. maltotetraose and maltotriose, are further split to give glucose, which can then be measured in known manner. For the measurement of the glucose formed in the presence of α-glucosidase, the hexokinase process is particularly preferred. The principle of this embodiment of the process according to the present invention can be illustrated by the following equations:

7 gluconate-6-P + 7NADH + 7H⁺

In the above equations, HK means hexokinase, NAD means nicotinamide-adenine-dinucleotide, NADH means the reduced form thereof, G-6-PDH means glucose-6-phosphate dehydrogenase and ATP means adenosine triphosphate.

For this embodiment of the present invention, i.e. the use of α-glucosidase there are also especially useful the maltoheptaose derivatives employed according to the present invention, i.e. compounds of general formula (I) in which R is other than a glucoside group. By the action of the two enzymes α-amylase and α-glucosidase, the substituent of R, i.e. a phenol group, a monoitrophenyl group or a dinitrophenyl group or the terminal sorbitol or gluconic acid residue, is split off and can easily be determined. The phenyl groups can be in the α- or β-position. In the case of the α-position, splitting off thereof takes place by the action of α-amylase and α-glucosidase alone and the substituted or unsubstituted phenols split off can then be easily determined by known color reactions. However, the present invention can also be employed in the case of β-positioned substituents, in which case, in addition to α-glycosidase, β-glucosidase is also employed.

In the case of the dinitrophenyl groups, the two nitro groups can be present in any desired position, for example as 2,4-, 2,6- or 3,5-substituents.

The nitrophenols or dinitrophenols liberated by the splitting off of the nitro group-containing substituents are themselves colored compounds which can easily be determined optically. If phenol itself is split off, then this can be determined by known methods, for example by reaction with a nucleophilic reagent, such as 3-methyl-6-sulphonylbenzthiazolone-hydrazone-(2) (HSK), in the presence of monophenol oxidase, a red colored material being formed which can be measured.

In the case of splitting off sorbitol, this can be oxidized, for example, by sorbitol dehydrogenase to give fructose and, at the same time, NAD present is reduced to NADH. The formation of NADH can then easily be determined in known manner with a UV spectrophotometer. If this is not available, then, by reaction with a tetrazolium salt, for example 2-(p-iodophenyl)-3-(p-nitrophenyl)-5-phenyl-tetrazolium chloride (INT), in the presence of diaphorase or some other electron carrier, a colored formazan is formed which can be measured in the visible spectrum.

In an analogous manner, liberated gluconic acid can be determined by known methods, for example with gluconate kinase, 6-phosphoglucate dehydrogenase and nicotinamide-adenine-dinucleotide phosphate (NADP), as well as optionally a tetrazolium salt and an electron carrier.

The process according to the present invention is generally carried out at a pH value of from 5 to 9. However, it is preferable to use a pH value of from 7 to 7.5 since, in this case, the best results are obtained in the shortest reaction times. If, according to the present invention, nitrophenyl compounds are employed, then the range of the most suitable pH values is somewhat narrower and is generally from 6 to 8.5.

The buffers used can be any of those which are effective in the main activity range of the enzymes employed. Preferred buffers include phosphate buffers, HEPES (N-(2-hydroxyethyl)-piperazine-N-2-ethane-sulphonic acid) and glycylglycine. The preferred buffer concentrations are from 10 to 200 mMol/liter.

The α-glucosidase is generally employed in an amount of from 0.1 to 5000 U/ml. It is a special advantage of the process according to the present invention that relatively large amounts of this enzyme can be used so that the α-amylase fission is the rate-determining step. It is, of course, also possible to employ even larger amounts of this enzyme but this provides no further advantages.

The compounds of general formula (I) employed according to the present invention are generally used in amounts of from 0.1 to 250 m/Mol/liter, amounts of from 0.5 to 100 mMol/liter being preferred.

Substrate saturation of the α-amylase with maltoheptaose is present at a concentration of 8 to 10 mMol. Therefore, it is preferable to use a minimum concentration of 8 mMol of maltoheptaose if it is desired to work under the conditions of substrate saturation, which is usually the case.

Furthermore, an activation agent for the α-amylase is preferably added. Such activation agents are known, the preferred ones including sodium chloride and potassium chloride.

In the case of another preferred embodiment of the process according to the present invention, the determination of the fission products takes place by reaction with maltose phosphorylase, with the formation of glucose-1-phosphate, which is then determined in known manner. According to a specially preferred embodiment, the glucose-1-phosphate is determined by conversion into glucose-6-phosphate by means of β-phosphoglucose mutase (β-PGLuM) and oxidation of the glucose-6-phosphate formed with NAD in the presence of glucose-6-phosphate dehydrogenase, with the formation of gluconate-6-phosphate and NADH, the formation of the latter being easily monitored photometrically. The measurement signal can be intensified by further oxidation with NAD in the presence of 6-phosphogluconate dehydrogenase with the formation of ribulose-5-phosphate and a further molecule of NADH.

The principle of this embodiment is illustrated by the following equations:

An advantage of this embodiment of the present invention is that maltose phosphorylase is more specific than α-glucosidase and, therefore, endogenic glucose does not disturb.

With regard to the buffer, there again applies what was stated above with regard to the embodiment of the present invention using α-glucosidase process.

Apart from the two above-mentioned embodiments of the process according to the present invention, the determination of the fragments formed from the maltoheptaose, i.e. maltotetraose, maltotriose and the maltose formed therefrom, can also take place by other methods known for this purpose.

The present invention also provides a reagent for the determination of α-amylase which comprises an α-amylase substrate and a system for the determination of a fission product formed from the α-amylase substrate by the α-amylase, the substrate used being a compound of general formula (I).

A preferred system for the determination of the fission products is the α-glucosidase system which contains α-glucosidase, an alkali metal chloride and a buffer. If the substrate consists of maltoheptaose itself, then, as enzymes, there are also necessary hexokinase (HK) and glucose-6-phosphate dehydrogenase (G6HPDH), as well as NAD, ATP and magnesium ions.

A reagent based upon the α-glucosidase system preferably comprises the following components:
$5 \times 10^3$ to $3 \times 10^4$ U/l. α-glucosidase,
$10^3$ to $5 \times 10^4$ HK,
$10^3$ to $5 \times 10^4$ G6PDH,
0.5 to 8 mM/l. NAD,
0.5 to 5 mM/l. ATP,
1 to 3 mM/l. $Mg^{2+}$,
25 to 100 mM/l. NaCl or KCl,
25 to 200 mM/l. buffer (pH 6.2 to 7.8) and
5 to 100 mM/l. maltoheptaose,
or a multiple or fraction thereof, in dry or dissolved form.

According to another preferred embodiment, the reagent comprises α-glycosidase, potassium chloride or sodium chloride, buffer and substrate. A reagent of this type comprises, in particular, $10^2$ to $5 \times 10^6$ U/l. α-glucosidase, 1 to 100 mMol/l. sodium chloride or potassium chloride, 10 to 250 mMol/l. buffer (pH 5 to 9) and 0.1 to 250 mMol/l. of a maltoheptaose derivative of general formula (I), referred to the concentration in the test. The reagent can be present in dry and especially in lyophilised form or also in the form of a solution, as a mixture of all components or separately.

According to a further embodiment of the reagent according to the present invention of the above-described type, α-glucosidase and/or phenol oxidase and HSK can additionally be present.

According to yet another embodiment of the reagent according to the present invention, in addition to α-glucosidase, sodium chloride or potassium chloride, buffer and substrate, it also contains sorbitol dehydrogenase and NAD or gluconate kinase, ATP, 6-phosphogluconic acid dehydrogenase and NADP, and optionally also a tetrazolium salt and diaphorase or phenazinemethosulphate (PMS).

A preferred reagent of this type comprises $1 \times 10^2$ to $3 \times 10^6$ U/l. α-glucosidase, $2 \times 10^3$ to $5 \times 10^4$ U/l. sorbitol dehydrogenase, $1 \times 10^3$ to $5 \times 10^4$ U/l. hexokinase, 0.5 to 50 mMol/l. ATP, 10 to 500 U/l. diaphorase (Chlostridium kluyveri), 0.01 to 0.5 mMol/l. tetrazolium salt, 0.1 to 10 mMol/l. NAD, 0.2 to 5 mMol/l. magnesium chloride, 0.5 to 20 mMol/l. maltoheptaitol 1 to 100 mMol/l. sodium chloride or potassium chloride and 10 to 250 mMol/l. buffer (pH 5.5 to 8.5).

If desired, a non-ionic surface-active agent can also be present, for example in an amount of from 5 to 50 mMol/l.

Another preferred embodiment of the reagent comprises 100 to $3 \times 10^6$ U/l. α-glucosidase, 10 to $10^4$ U/l. 6-phosphogluconate dehydrogenase, 20 to $2 \times 10^4$ U/l. gluconate kinase, 0.5 to 25 mMol/l. ATP, 0.05 to 10 mMol/l. NADP, 1.0 to 20 mMol/l. maltoheptagluconic acid, 0.5 to 5 mMol/l. magnesium chloride, 1 to 100 mMol/l. sodium chloride and 10 to 250 mMol/l. buffer (pH 5.5 to 8.5).

Yet another reagent according to the present invention comprises 0.1 to 250 mMol/l, α-nitrophenylmaltoheptaoside or dinitrophenyl-maltoheptaoside, $1 \times 10^2$ to $2.5 \times 10^6$ U/l. α-glucosidase, 1 to 100 mMol/l. sodium chloride or potassium chloride and 10 to 250 mMol/l. phosphate buffer (pH 7.0 to 8.0).

Yet another embodiment of the reagent according to the present invention comprises:
0.1 to 250 mMol/l. α-phenylmaltoheptaoside,
$1 \times 10^2$ to $1.5 \times 10^6$ U/l. α-glucosidase,
10 to $10^5$ U/l. monophenol oxidase,
0.1 to 10 mMol/l. HSK,
1 to 100 mMol/l. sodium chloride or potassium chloride,
10 to 250 mMol/l. buffer.

Another preferred system for the determination of the fission products is the maltose phosphorylase system which consists essentially of maltose phosphorylase, β-phosphoglucomutase βPGluM, glucose-6-phosphate dehydrogenase (G6PDH), glucose-1,6-diphosphate (G1,6DP), NAD, buffer, maltoheptaose and optionally 6-phosphogluconate dehydrogenase (6PGDH).

An especially preferred reagent with this detection system comprises:
$0.5 \times 10^3$ to $2 \times 10^4$ U/l. maltose phosphorylase,
$1 \times 10^2$ to $1 \times 10^4$ β-PGLuM,
$2 \times 10^3$ to $3 \times 10^4$ U/l. glucose-6-phosphate dehydrogenase,
0.5 to 10 mMol/l. NAD,
0.002 to 1 mMol/l. glucose-1,6-diphosphate,
0.5 to 100 mMol/l. buffer (pH 6.0 to 7.5),
5 to 50 mMol/l. maltoheptaose and optionally
$1 \times 10^2$ to $1 \times 10^4$ U/l. 6-phosphogluconate dehydrogenase.

The reagent according to the present invention can be present in dry or dissolved form and it can also be impregnated or incorporated into a sheet-like carrier, for example a film, an absorbent paper or the like. In the latter case, it preferably consists of at least three layers or laminae, the first of which contains the substrate, the second of which serves as a barrier layer and the third of which contains the system for the determination of the fission products. If such a multi-layer reagent material, which can be used for a simple rapid test for α-amylase, is brought into contact with a liquid α-amylase-containing sample, then the α-amylase splits the substrate and the fragments diffuse through the intermediate layer into the third layer containing the determination system. As detection reaction, in this case there is preferably employed a color-formed reaction in order to make visible the concentration of the α-amylase on the basis of the resultant coloration if the fission products themselves are not already colored.

The maltoheptaose derivatives employed according to the present invention can be prepared in various ways. In the case of the phenylated derivatives, there can be used not only chemical but also, enzymatic methods. The chemical syntheses are, in principle, based upon the reaction of peracetylated maltoheptoase with the appropriate phenol in the presence of a Friedel- Crafts catalyst. This method can be used not only for phenol itself but also for mononitrophenol and dinitrophenol. On the other hand, it is also possible first to prepare the phenyl derivative and subsequently to nitrate it, for example with the use of the process described in Bull. Chem. Soc. Japan, 34, 718/1961. This method is particularly suitable for the mononitro derivative. Under certain circumstances, a separation of the resultant o and p-nitrophenyl derivatives can also be carried out.

This reaction is preferably carried out by melting or boiling under reflux in non-polar solvents with zinc chloride, stannic chloride or titanium tetrachloride as Friedel-Crafts catalyst. After the introduction of the phenol or nitrophenol, the protective groups are split off in known manner, for example with sodium methylate, ammonia, potassium hydroxide or barium methoxide, in each case in methanolic solution, or with aqueous barium hydroxide solution or the like.

The enzymatic preparation of the phenyl derivatives can take place by transglucosidation of the phenyl glycoside or of the corresponding nitrated phenyl glucoside with α-cyclodextrin, amylase or soluble starch in the presence of a specific microbial transferase. For this purpose, it is preferred to use a transferase from Bacillus macerans. In this case, there can be used for this transglucosidation the known amylase from Bacillus macerans (E.C., 2.4.1.19.DSM 24; isolation see J. A. de Pinto, L. L. Campbell, Biochemistry, 7, 114/1968; transfer reaction see Methods in Carbohydrate Chemistry, Vol. II, 347 (1963)) which besides its hydrolytic and cyclising action, clearly also displays a glucosyl-transferring effectiveness.

Those compounds of general formula (I) in which R is a sorbitol residue can be obtained from maltoheptaose by reduction with sodium borohydride under mild conditions.

Finally, the compounds of general formula (I) in which R is a gluconic acid group can be prepared chemically or enzymatically by methods known for the preparation of gluconic acid from maltoheptaose, for example by oxidation with bromine (see Methods in Carbohydrate Chemistry, Vol. II, 13 (1963)).

As already mentioned, the present invention not only provides a rapid and specific process for the determination of α-amylase but also completely or substantially removes the lag phase, which is of particular importance when the process is used in automatic analysers. Furthermore, the process according to the present invention can be carried out in many embodimental forms without the use of complicated apparatus for the evaluation and is, therefore, especially useful for rapid diagnostics and for optical determination in the visible range of light. However, at the same time, the various embodiments of the process according to the present invention can also be determined with UV measurement devices. Further advantages are the strict proportionality and the absence of disturbance by chemically related components of the blood.

The substrates employed according to the present invention are readily obtainable in a high state of purity. A simple process for the preparation of maltoheptaose is described in German Patent Specification No. P 27 41 191.2. The process can be used for the determination of α-amylase in biological fluids, such as serum, heparin plasma, urine and the like, as well as in other liquid and solid materials.

The following Examples are given for the purpose of illustrating the present invention:

EXAMPLE 1

Maltogen method (α-glycosidase system)

A reagent mixture containing α-glucosidase, G6PDH, HK, NAD, ATP, maltoheptaose, magnesium ions, sodium chloride and phosphate buffer is dissolved in 2.0 ml. distilled water. The storage stability of the reagent at ambient temperature is about 1 hour and at temperatures below 8° C. is 6 hours.

The solution obtained contains the following concentrations of the reagents:

| | |
|---|---|
| phosphate buffer | 50 mMol/l.; pH 7.0 |
| sodium chloride | 50 mMol/l. |
| magnesium ions | 2 mMol/l. |
| maltoheptaose | 10 mMol/l. |
| ATP | 1.2 mMol/l. |
| NAD | 2 mMol/l. |
| HK | $\leq 2$ U/l. |
| G6PDH | $\leq 2$ U/l. |
| α-glucosidase | $\leq 10$ U/l. |

The solution is mixed at 25° C. with 0.02 ml. serum sample, filled in a cuvette of 1 cm. path length and then the absorbance determined at 365 nm, 340 nm or 334 nm in a photometer. After 10 minutes, the extinction is read off and then, at intervals of one minute, reading off is repeated five times.

From the absorbance differences per minute (ΔA/min.) there is determined the average value, the reagent blank value is subtracted and the corrected value used for the calculation. The calculation is made as follows:

| | |
|---|---|
| U/l. (25° C.) = 4244 × ΔA/min. | [365 nm] |
| = 2290 × ΔA/min. | [340 nm] |
| = 2335 × ΔA/min. | [334 nm] |

Figure 1:
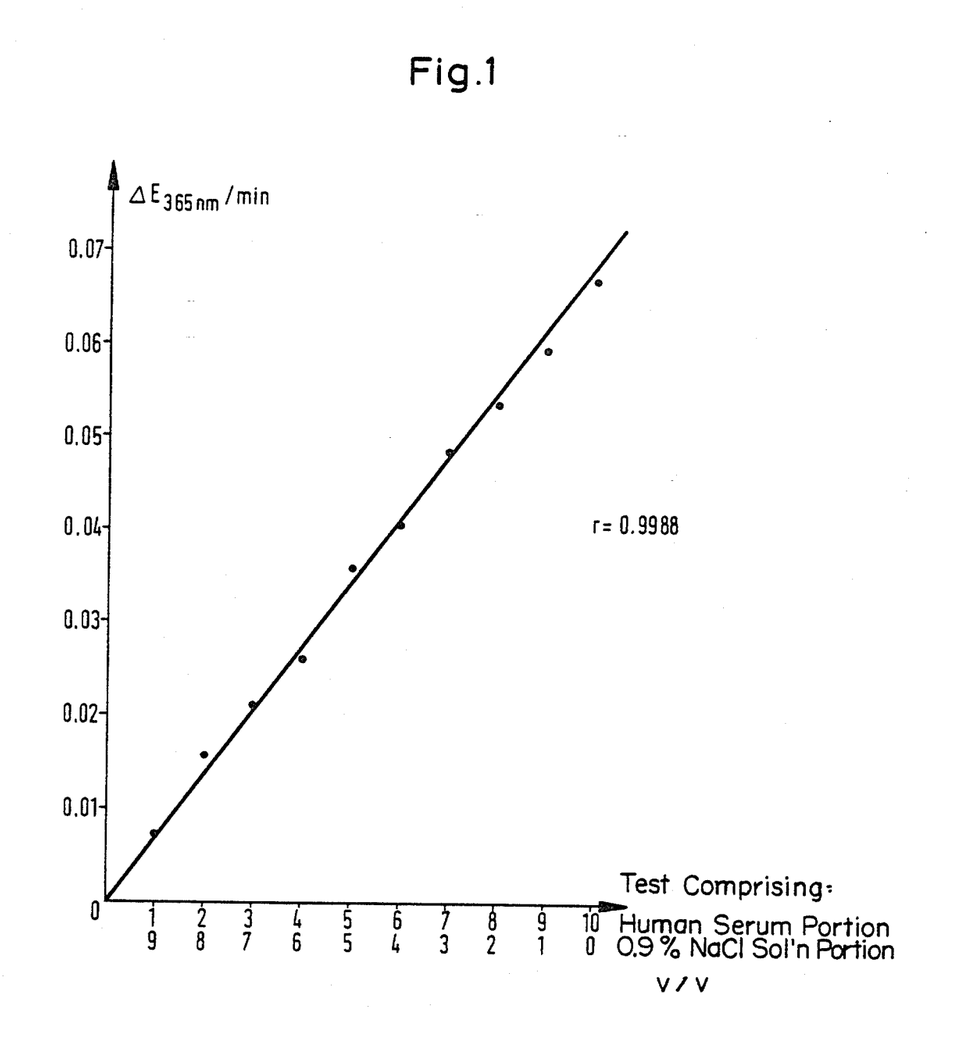

The FIGURE of the accompanying drawings shows the results obtained with a series of dilutions of human serum with physiological saline solution using this method.

If the reagent is divided up into two batches, one of which contains the maltoheptaose and the other the mixture of all the other reagents, then the storage stability of the solutions produced therewith can be increased. For the mixture of the reagents at temperatures of up to 8° C., the stability is up to 30 hours and at ambient temperature is about 8 hours. The corresponding storage stability of the maltoheptaose solution is 6 weeks and about 1 month, respectively.

EXAMPLE 2

Determination with the maltose phosphorylase system

Two reagents are prepared consisting of the amylase substrate and the maltose phosphorylase system. One reagent contains the maltoheptaose substrate and the other contains soluble starch according to the prior art. After dissolving in water, the reagent concentration is as follows:

| | according to the invention | comparison |
|---|---|---|
| phosphate buffer | 20 mM; pH 6.5 | 20 mM; pH 6.5 |

-continued

| | according to the invention | comparison |
|---|---|---|
| NAD | 2 mM | 2 mM |
| maltoheptaose | 10 mM | — |
| soluble starch | — | 5 mg./ml. |
| glucose-1,6-diphosphate | traces | traces |
| maltose phosphorylase (micro-organism) | 3 U/l. | 3 U/l. |
| β-phosphoglucomutase (micro-organism) | 1 U/l. | 1 U/l. |
| G6PDH (*Leuconostoc mesenteroides*) | 9 U/l. | 9 U/l. |
| 6PGDH (*Leuconostoc mesenteroides*) | 1 U/l. | 1 U/l. |

The solution obtained is incubated at 30° C., mixed with the sample solution and the absorbance difference measured in a photometer at Hg 334 nm. After a pre-incubation period of 10 minutes, the extinction difference is measured over a period of 10 minutes. For 2.0 ml. of reagent and 0.10 ml. of sample, there is then given the following calculation formula:

$$\Delta E/\text{min.} \times \frac{2.1 \times 1000}{6.18 \times 0.1 \times 2.0} = \Delta E/\text{min.} \times 1699 \ U/l.$$

In the case of the use of five different human sera, the following values are found with the above reagents:

| serum | present invention | starch |
|---|---|---|
| 1 | 37.4 U/l. | 15.3 U/l. |
| 2 | 61.2 U/l. | 27.3 U/l. |
| 3 | 95.1 U/l. | 39.1 U/l. |
| 4 | 114 U/l. | 44.2 U/l. |
| 5 | 374 U/l. | 161 U/l. |

EXAMPLE 3

Preparation of α-phenylmaltoheptaoside (a) Tridecosacetyl-β-D-maltoheptaose 57.6 g. (50 mM) maltoheptaose and 41 g. (500 mM) anhydrous sodium acetate are suspended in 543 ml. (5.75 mole) acetic anhydride and vigorously stirred at 100° C. for 4 hours, with the exclusion of moisture. After cooling to about 60° C., the reaction mixture is stirred into about 1 liter ice water and further stirred overnight at 4° C., a viscous, semi-crystalline mass thereby precipitating out. After pouring off the supernatant, the residue is again stirred with ice water, the product thereby crystallising through. It is separated off, washed and dried. There are obtained 80.7 g. (76% of theory) tridecosacetyl-β-D-maltoheptoase in the form of colorless crystals: $[\alpha]_D^{RT} = +137.5°$ (c.=1.15 chloroform); m.p. 150° C. (not sharp) (RT means ambient temperature).

The mother liquor (the decantate) is evaporated to dryness in a vacuum and the residue triturated with water and brought to crystallization. There are obtained a further 22.3 g. of product; $[\alpha]_D^{RT} = 136°$ (c=1, chloroform); m.p. 150° C.

Thus, the total yield of product is 103 g. ($\hat{=}97\%$ of theory).

The product can be recrystallized from ethanol until, after repeated recrystallizations, the melting point and optical rotation do not change. Therefore, the product is, on the $C_1$ atom, of optically uniform configuration (β).

(b) Dodecosacetyl-α-phenyl-D-maltoheptaoside 9.54 g (4.5 mM) Tridecosacetyl-β-D-maltoheptaose, 0.61 g. (4.5 mM) freshly melted zinc chloride and 4.23 g. (45 mM) distilled phenol are stirred for 2.5 hours at 100° C. with the exclusion of moisture. While still warm, the reaction mixture is dissolved in ethyl acetate and washed twice with 100 ml. amounts of water, three times with 100 ml. 1N aqueous sodium hydroxide solution, once with 100 ml. 1N acetic acid and once with 100 ml. saturated aqueous sodium chloride solution, the initially brown solution thereby becoming pale yellow. After drying over anhydrous magnesium sulphate, the solution is evaporated to dryness and taken up in 30 ml. warm methanol. After standing overnight, a syrupy material separates out which is crystallized from ethanol. There are obtained 8.7 g. dodecosacetyl-α-phenyl-D-maltoheptaoside (90% of theory); m.p. 155°–165° C. (decomp.); $[\alpha]_D^{RT} = +147°$ (c=8 in chloroform).

(c) Phenyl-α-D-maltoheptaoside 10.8 g. (5 mM) Peracetyl-1-phenyl-α-D-maltoheptaoside are dissolved in 200 ml. warm anhydrous methanol and mixed at ambient temperature, with the addition of some dioxan, while stirring with 30 ml. 0.1N sodium methylate solution and then stirred at ambient temperature for 16 hours. After 20 minutes, the product begins to separate out in semi-crystalline form. Finally, it is mixed with 200 ml. acetone, cooled to 4° C. and filtered off with suction. The product is dissolved in 160 ml. water, decolorised with active charcoal and desalinated with a cation exchange resin (Dowex 50 H+). There are obtained 5.6 g (91% of theory) phenyl-α-D-maltoheptaoside in the form of a colorless lyophilisate; $[\alpha]_D^{RT} = +176°$ (c=10 in water).

The product still contains some free maltoheptaose and, according to HPLC analysis (detection at 254 nm), also 2 UV-positive impurities. These are removed by chromatography on cross-linked dextran (Sephadex LH 20), using water as elution agent.

EXAMPLE 4

Preparation of p-nitrophenyl-α-D-maltoheptaoside (a) Peracetyl-p-nitrophenyl-α-D-maltoheptaoside 13.6 g. (20 mM) Peracetyl-maltoheptaose, prepared in the manner described in Example 3(a), are dissolved in 90 ml. anhydrous benzene, together with 11.9 g. (100 mM) p-nitrophenol and mixed, while stirring and with the exclusion of moisture, with 10.4 g. (4.5 ml.; 40 mM) $SnCl_4$. A voluminous mass thereby precipitates out which, however, dissolves again upon heating. The reaction mixture is boiled under reflux for 1 hour. Upon cooling, a viscous mass precipitates out which, after the addition of 80 ml. ethyl acetate, again goes into solution. Upon stirring the solution into 180 ml. 2N aqueous sodium carbonate solution, $SnO(OH)_2$ precipitates out. This is separated off, with the addition of some active charcoal. The aqueous phase is separated off and the organic phase well washed, finally with a saturated aqueous solution of sodium chloride. After drying and evaporating the solution, there is obtained a resinous product which is crystallized from ethanol. There are obtained 6.2 g. (41% of theory) peracetyl-p-nitophenyl-α-D-maltoheptaoside; m.p. 100° C. (decomp.); $[\alpha]_D^{RT} = +131°$ (c=1 in chloroform).

The same product is also obtained when the reaction is carried out in chloroform or when the reaction is carried out with titanium tetrachloride instead of with stannic chloride.

(b) p-Nitrophenyl-α-D-maltoheptaoside 5.5 g (7 mM) Peracetyl-p-nitrophenyl-α-D-maltoheptaoside is slurried in 100 ml. anhydrous methanol and mixed with 5 ml. of an approximately 1N sodium methylate solution. The starting material becomes honey-like and dissolves slowly. After some time, the crystalline deposition of the de-acetylated product commences which, after stirring overnight, is complete. It is filtered off with suction, washed with methanol and dried. There are obtained 2.8 g. (86% of theory) p-nitrophenyl-α-D-maltoheptaoside; $[\alpha]_D^{RT} = +124°$ (c=0.6 in water).

The product is purified on cross-linked dextran (Sephadex LH20), using water as elution agent. There are obtained 1.2 g. (45% of theory) of the above-described compound which is active in the enzymatic test. Furthermore, the compound is also obtainable by the nitration of α-phenylmaltoheptaoside, obtained according to Example 1, with nitrating acid in the manner described in Bull. Chem. Soc. Japan, 34, 717(1961).

When using dinitrophenol instead of mononitrophenol, the corresponding dinitrophenyl compound is obtained.

EXAMPLE 5 p-Nitrophenyl-α-maltooligosaccharides by enzymatic synthesis with Bacillus macerans amylase (E.C.2.4.1.19 from Bac. mac. DSM 24)

In addition to a hydrolytic and cyclising action, *Bacillus macerans* amylase also has glycosyl-transferring properties which can be utilised for the synthesis of oligosaccharides and derivatives thereof (see Methods in Carbohydrate Chemistry,II,347(1963)). For the synthesis of p-nitrophenyl-oligosaccharides, this process was optimised in the following manner:

680 mg. *Bacillus macerans* amylase (E.C. 2.4.1.19 from *Bac. mac.* DSM 24) (lyophilisate) (0.46 U/mg. weighed amount, protein content of the weighed amount 28.5%, free from p-nitrophenyl-α-D-glucoside-splitting activities), 400 mg. α-D-p-nitrophenylglucoside, 3.5 g. α-cyclodextrin and 70 ml. Soerensen phosphate buffer (pH 6.2; 0.01M) are mixed. The batch is incubated for 24 hours at 37° C. For purification, α-cyclodextrin and formed β-cyclodextrin are first separated off by means of the tetrachloroethylene inclusion compound. After chromatography on cross-linked dextran (Sephadex LH20), there are obtained 50 mg. of lyophilisate of p-nitrophenylmaltoheptaoside, which is highly active in the amylase assay.

EXAMPLE 6

Preparation of maltoheptaitol 10 g. Maltoheptaose are dissolved in 50 ml. water, 2 g. sodium borohydride are added thereto portionwise and the reaction mixture is stirred for 75 minutes at ambient temperature till test for reducing sugar is negative). Sodium ions are removed by chromatography on a cation exchange resin (Dowex 50 H+) (pH value of the solution after passage through the exchange resin=3.5). The eluates from the exchange resin are evaporated in a vacuum and taken up and evaporated several times with methanol/water (addition of water for dissolving the product) for the removal of boric acid as methyl ester. The solution obtained, which is finally neutral, is lyophilised. There are obtained 9 g. (90% of theory) maltoheptaitol, which is free of reducing sugars.

| Content (determined enzymatically) | by glucose | 86.1% |
| --- | --- | --- |
| | by sorbitol | 89.0% |
| | water | 8.5% |

EXAMPLE 7

Preparation of maltoheptagluconic acid

11.5 g. (0.01 mole) Maltoheptaoase and 6 g. barium benzoate are dissolved in 150 ml. water. While stirring and cooling, 1 ml. bromine is added thereto and stirring continued for 36 hours. After driving off excess bromine by means of nitrogen, the reaction mixture is mixed with 4 ml. 4N sulphuric acid and some active charcoal, filtered and the filtrate extracted with chloroform in order to remove benzoic acid. The aqueous solution is mixed with 3.2 g. silver carbonate and stirred (pH: neutral). The insoluble salts are filtered off and the clear solution passed over 20 ml. Amberlite JR H+. The acidic eluate is immediately neutralized with sodium hydroxide and lyophilised. There are obtained 8 g. (72% of theory) maltoheptagluconic acid.

| Content (determined enzymatically) | by glucose | 85% |
| --- | --- | --- |
| | by gluconic acid | 80% |
| | water | 9.3% |

EXAMPLE 8

Detection of α-amylase with phenyl-α-maltoheptaoside as substrate

Phenyl-α-maltoheptaoside is split with α-amylase into phenyl-α-maltotriglucoside or -tetraglucoside which is converted by α-glucosidase into phenol and glucose. The liberated phenol is oxidatively coupled by monophenol oxidase with the nucleophilic reagent 3-methyl-6-sulphonyl-benzthiazolone-hydrazone-(2) (HSK) to give a red coloured material, the rate of formation of which is proportional to the amylase activity in the sample and can be monitored photometrically. Test principle:

Measurement conditions: 25° C., measurement wavelength 492 nm, 1 cm. cuvette; the following Table shows the composition of the reagent:

TABLE

| reagent | concentration in the test |
| --- | --- |
| phosphate buffer, pH 7.4 | 0.05 mol/l. |
| sodium chloride | 0.05 mole/l. |

| reagent | concentration in the test |
| --- | --- |
| phenyl-α-D-maltoheptaoside | 10 mMole/l. |
| HSK | 1 mMole/l. |
| monophenol oxidase | 1 U/ml. |
| α-glucosidase | 10 U/ml. | test volume: 2.0 ml.

Instead of phosphate buffers, glycine, glycylglycine, Hepes, tris, tra and other buffers have also proved to be useful.

EXAMPLE 9

Determination of α-amylase with p-nitrophenyl-malto-heptaoside

Test principle:

After splitting the maltoheptaoside, the fission products are broken down into glucose and p-nitrophenol. The p-nitrophenolate ion has a yellow color in alkaline solution and can, therefore, be directly measured optically.

Test system:
Reaction mixture:
50 mM/l. phosphate buffer, pH 7.4
50 mM/l. sodium chloride
5 to 50 U/ml. α-glucosidase
5 to 10 mM/l. p-nitrophenyl-α-maltoheptaoside.

Test batch:
1 ml. reaction mixture + 50 μl. sample (serum)
temperature: 30° C.
wavelength: 405 nm
Serum start after achieving the measurement temperature (10 minutes pre-incubation).

EXAMPLE 10

α-Amylase determination with maltoheptaitol

Test principle:

(SDH = sorbitol dehydrogenase)

Test system:

| reaction batch | ml. | concentration in test |
| --- | --- | --- |
| Na—/K—PO₄ buffer 0.02 mol/l. + Triton X100 2 ml./100 ml. + NaCl 10 mMol/l., pH 6.9 | 1.92 | 12.8 mMol/l. PO₄³⁺ 6.4 mMol/l. |
| MgCl₂ 0.3 mol/l. | 0.01 | 1.0 mMol/l. |
| maltoheptite 100 mMol/l. | 0.10 | 3.3 mMol/l. |
| NAD, C = 40 mg./ml. | 0.05 | 1.0 mMol/l. |
| INT, c = 0.6 mg./ml. | 0.20 | 0.09 mMol/l. |
| diaphorase (Clostr. kluyveri) 5 mg./ml. + | 0.05 | 167 U/l. |
| ATP, c = 50 mg./ml. | 0.10 | 3.29 mMol/l. |
| hexokinase 280 U/ml. + | 0.05 | 4666 U/l. |
| SDH 180 U/ml. + | 0.30 | 18000 U/l. |
| α-glucosidase 1120 U/ml. + | 0.20 | 74670 U/l. |
| sample (serum) | 0.02 | |

+ in the test buffer

Start by adding sample: measurement is performed at 492 nm; temperature: 25° C.

EXAMPLE 11

α-Amylase determination with maltoheptagluconate

Test principle:

maltotrigluconate + maltotetraose ribulose-5-P + NADPH + CO₂ + H⁺

Test system:

| reaction batch | ml. | concentration in test |
| --- | --- | --- |
| Na—/K—PO₄ buffer 0.02 mol/l. + NaCl 10 mMol/l., pH 6.9 | 2.19 | 14.6 mMol/l. phosphate 7.3 mMol/l.NaCl |
| MgCl₂ 1 mol/l. | 0.01 | 3.3 mMol/l. |
| maltoheptagluconic acid 150 mMol/l. | 0.10 | 5 mMol/l. |
| NADP, c = 10 mg./ml. | 0.10 | 0.38 mMol/l. |
| ATP, c = 50 mg./ml. | 0.10 | 2.7 mMol/l. |
| gluconate kinase 40 U/ml. | 0.03 | 1066 U/l. |
| 6-phosphogluconate dehydrogenase 24 U/ml. | 0.10 | 800 U/l. |
| α-glucosidase 1120 U/ml. | 0.30 | 11.2 × 10⁴ U/l. |
| sample (serum) | 0.02 | |

Start by adding sample; measurement is performed at 340 nm or 365 nm; temperature: 25° C.; test volume: 3.00 ml.

It will be understood that the specification and examples are illustrative but not limitative of the present invention and that other embodiments within the spirit and scope of the invention will suggest themselves to those skilled in the art.

What is claimed is:

1. In a process for the determination of alpha-amylase by the enzymatic splitting of an alpha-amylase substrate and measurement of a fission product, the improvement comprising using, as a substrate, an enzymatically produced maltoheptaose compound of the formula in which
R is a phenylglucoside, mononitrophenyl-glucoside, dinitrophenylglucoside, and wherein the sugar moiety of the R radical is substituted in the alpha-configuration,
in combination with alpha-glucosidase.

2. Process as claimed in claim 1, wherein said reaction is carried out at a pH value from 5 to 9.

3. Process as claimed in claim 1, wherein 0.1 to 250 mMol/l. of said maltoheptaose compound are used.

4. Process as claimed in claim 3, wherein 0.5 to 100 m/Mol.l. of the maltoheptaose compound are used.

5. Process as claimed in claim 1, wherein R is a phenylglucoside group.

6. Process as claimed in claim 5, wherein the phenol fission product is determined with 3-methyl-6-sulphonylbenzthiazolone-hydrazone-(2) in the presence of monophenol oxidase, as a measure of the initial α-amylase content.

7. Composition for use in determination of the presence or lack thereof of alpha amylase comprising an enzymatically produced maltoheptaose compound of claim 1 and a substance which determines the presence of fission products formed by action of alpha amylase on said maltoheptaose.

8. Composition as claimed in claim 7, consisting essentially of alpha-glucosidase, hexokinase, glucose-6-phosphate dehydrogenase, NAD, ATP, magnesium ions, NaCl, phosphate buffer and an enzymatically produced maltoheptaose as substrate.

9. Reagent as claimed in claim 8 comprising:
$5 \times 10^3$ to $3 \times 10^4$ U/l. Alpha-glucosidase,
$10^3$ to $5 \times 10^4$ U/l. hexokinase,
$10^3$ to $5 \times 10^4$ U/l. glucose-6-phosphate dehydrogenase,
0.5 to 8 mMol/l. NAD,
0.5 to 5 mMol/l. ATP,
1 to 3 mMol/l. magnesium ions,
25 to 100 mMol/l. sodium chloride or potassium chloride,
25 to 100 mMol/l. buffer (pH 6.2 to 7.8) and
5 to 100 mMol/l. an enzymatically produced maltoheptaose in dry or dissolved form.

10. Composition as claimed in claim 7, further comprising alpha glucosidase, sodium chloride or potassium chloride, buffer, and an enzymatically produced maltoheptaose.

11. Composition as claimed in claim 10, comprising:
$10^2$ to $5 \times 10^6$ U/l. α-glucosidase,
1 to 100 mMol/l. sodium chloride or potassium chloride,
10 to 250 mMol/l. buffer (pH 5 to 9), and
0.1 to 250 mMol/l of an enzymatically produced maltoheptaose compound.

12. Reagent as claimed in claim 10, which additionally contains at least one of β-glucosidase, phenol oxidase and 3-methyl-6-sulphonyl-benzthiazolone-hydrazone-(2).

13. Reagent as claimed in claim 10, which additionally contains sorbitol dehydrogenase or gluconate kinase and 6-phosphogluconate dehydrogenase, and NAD.

14. Reagent as claimed in claim 13, which contains in addition a tetrazolium salt, diaphorase or PMS.

15. Reagent as claimed in claim 13, wherein the reagents are impregnated or incorporated into a sheet-like carrier material.

16. Reagent as claimed in claim 7, also containing a surface-active agent.

17. Reagent as claimed in claim 7, consisting essentially of maltase phosphorylase, alpha-phosphoglucomutase, glucose-6-phosphate dehydrogenase, glucose-1, 6-diphosphate, NAD, buffer, and as a substrate an enzymatically produced maltoheptaose.

18. Composition as in claim 7, wherein said substance is maltose phosphorylase.

19. In a process for the determination of alpha-amylase by the enzymatic splitting of an alpha-amylase substrate and measurement of a fission product, the improvement comprising using a substrate consisting essentially of an alpha substituted maltoheptaose compound of the formula wherein
R is a phenylglucoside, mononitrophenyl-glucoside, dinitrophenylglucose, and wherein the sugar moiety of the R radical is substituted in the alpha-configuration,
in combination with alpha-glucosidase.

* * * * *

UNITED STATES PATENT AND TRADEMARK OFFICE
CERTIFICATE OF CORRECTION

PATENT NO.   : 4,544,631
DATED        : October 1, 1985
INVENTOR(S)  : Elli Rauscher et al It is certified that error appears in the above-identified patent and that said Letters Patent is hereby corrected as shown below:

Column 2, line 16: change "phenylglycoside" to --phenylglucoside--.

Column 3, line 25: change "$\alpha$-glycosidase" to --$\alpha$-glucosidase--.

Column 5, line 19: change "G6HPDH" to --G6PDH--.

Column 5, line 35: change "$\alpha$-glycosidase" to --$\alpha$-glucosidase--.

Column 6, line 38: change "0.002" to --0.001--.

Column 8, line 5: change "$\alpha$-glycosidase" to --$\alpha$-glucosidase--

Column 8, lines 21-23 in the right column, "$\leq$" should be --$\geq$--.

Signed and Sealed this

First Day of April 1986

[SEAL]

Attest:

DONALD J. QUIGG

Attesting Officer

Commissioner of Patents and Trademarks